(12) United States Patent
Hansen

(10) Patent No.: US 8,748,190 B2
(45) Date of Patent: Jun. 10, 2014

(54) METHODS FOR DETECTING URUSHIOL-BEARING PLANTS SUCH AS POISION IVY

(76) Inventor: Alisha Hansen, Sedona, AZ (US)

( * ) Notice: Subject to any disclaimer, the term of this patent is extended or adjusted under 35 U.S.C. 154(b) by 0 days.

(21) Appl. No.: 12/731,605

(22) Filed: Mar. 25, 2010

(65) Prior Publication Data

US 2010/0248381 A1      Sep. 30, 2010

Related U.S. Application Data

(60) Provisional application No. 61/163,271, filed on Mar. 25, 2009.

(51) Int. Cl.
*G01N 33/52* (2006.01)
*G01N 21/78* (2006.01)
*G01N 33/00* (2006.01)
*G01N 31/22* (2006.01)

(52) U.S. Cl.
CPC ............ *G01N 33/0098* (2013.01); *G01N 33/52* (2013.01); *G01N 21/78* (2013.01); *G01N 31/22* (2013.01)
USPC .......................................... 436/131; 436/164

(58) Field of Classification Search
None
See application file for complete search history.

(56) References Cited

U.S. PATENT DOCUMENTS

| | | | |
|---|---|---|---|
| 4,259,318 | A | 3/1981 | Duhe et al. |
| 4,472,507 | A | 9/1984 | Pluim, Jr. |
| 5,588,972 | A | 12/1996 | Patil et al. |
| 5,767,109 | A | 6/1998 | Sanchez et al. |
| 2006/0147341 | A1 | 7/2006 | Jahngen et al. |

FOREIGN PATENT DOCUMENTS

WO    WO-2009/139864 A2 * 11/2009

OTHER PUBLICATIONS

Parke, D. "Application of p-Toluidine in Chromogenic Detection of Catechol and Protocatechuate, Diphenolic Intermediates in Catabolism of Aromatic Compounds," Applied and Environmental Microbiology, 1992, 58, 2694-2697.*

Andrews Hay "Ammonium Sulfamate" submitted Jun. 26, 2003 to "Poison Ivy, Oak, & Sumac Information Center" website at <http://poisonivy.aesir.com/view/control.html>; archived on Feb. 14, 2004 at <http://web.archive.org/web/20040214001016/http://poisonivy.aesir.com/view/control.html>.*

Yin Tao et al., Oxidation of Benzene to Phenol, Catechol, and 1,2,3-Trihydroxybenzene by Toluene 4-Monooxygenase of Pseudomonas mendocina KR1 and Toluene 3-Monooxygenase of Ralstonia Pickettii PKO1, Appl. and Env. Microbiol., Jul. 2004, 3814-3820.

Fujita, Y. et al., A color reaction of 1,2 diphenols based on colored complex formation with phenylfluorone and iron (III) and its application to the assay of catecholamines in pharmaceutical preparations, Chem. Pharm. Bull., 33, 5385-5392 (1985).

Howard S. Mason and E. W. Patterson, the Reaction of Quinones with Protamine and Nucleoprotamine: N-Terminal Proline, J. Biol. Chem., 212(1), 485-496 (1955).

Uchiyama et al., Formation of a stable adduct between 1,2 benzoquinone and dimethylamine and its application to the spectrophotometric determination of 1,2-benzoquinone, Anal. Chim. Acta, 351(1-3), 259-264 (1997) (abstract).

Luca Valgimigli et al., Photometric assay for polyphenol oxidase activity in olives, olive pastes and virgin olive oils, J. Amer. Oil Chemists' Soc., 78(12), 1245-1248 (2001), (abstract).

* cited by examiner

*Primary Examiner* — Yelena G Gakh
*Assistant Examiner* — Michelle Adams
(74) *Attorney, Agent, or Firm* — McDonnell Boehnen Hulbert & Berghoff LLP

(57) ABSTRACT

The present invention provides methods for detecting urushiol-bearing plants such as poison ivy, poison oak, and poison sumac. Accordingly, one aspect of the invention is a method of detecting a urushiol-bearing plant, the method comprising: dispensing a urushiol marking composition on a surface of the urushiol-bearing plant; then detecting a visual change on the urushiol-bearing plant caused by the reaction of the urushiol marking composition with the urushiol borne by the urushiol-bearing plant.

19 Claims, No Drawings

METHODS FOR DETECTING URUSHIOL-BEARING PLANTS SUCH AS POISION IVY

CROSS-REFERENCE TO RELATED APPLICATIONS

This application claims the priority of U.S. Provisional Patent Application Ser. No. 61/163,271, filed Mar. 25, 2009, which is hereby incorporated herein by reference in its entirety.

BACKGROUND OF THE INVENTION

1. Field of the Invention

The present invention relates generally to the detection of harmful plants. The present invention relates more particularly to methods for detecting urushiol-bearing plants such as poison ivy, poison oak, and poison sumac.

2. Technical Background

Urushiol is an oily mixture of catechol compounds having long chain alkyl or alkenyl substitution at their 3-positions. It occurs in the sap and resin of the leaves, vines and roots of a number of common plants, and can be released to the plant surface when fragile plant parts are cut or bruised. Urushiol can stay active for up to five years after release from the plant.

Many commonly-occurring plants bear urushiol. For example, poison ivy (*Toxicondendron radicans*) grows throughout the United States, primarily east of the Rockies. It can be a vine or shrub, and its most common leaf pattern is in groups of three with notched edges. Leaves are red in the spring, green in the summer, and can be a variety of colors with white berries in the fall. Poison oak (*Toxicondendron diversilobum*) grows predominantly west of the Rockies in the United States. It is typically a small bushy plant or climbing vine with leaves in groups of three, five or seven. It also changes leaf color throughout the season, with white berries present in the fall. Poison sumac (*Toxicondendron vernix*) is most common in the boggy areas of the south and northeast regions of the United States. It is a bush with seven to thirteen feather-like leaves per stem. It looks very similar to its non-toxic relative. The only way to distinguish the poisonous variety from the benign variety in the field is the color of the berries that appear during the fall; poison sumac has green berries, while sumac has red berries. There are a number of other urushiol bearing plants, each with a different appearance and range.

Urushiol can cause strong to severe allergic dermatitis, known as Rhus dermatitis, in humans. Direct skin-to-plant contact is the most frequent cause of exposure to urushiol, but it can also be indirectly transferred to skin via clothing, animal fur, garden tools and shoes. Rhus dermatitis typically begins with severe itching 8-48 hours after contact. The rash appears as red patches or small blisters progressing into red weeping blisters, and can last for three weeks if untreated. Urushiol contact can cause more severe reactions as well. For example, forestry workers and firefighters in the West can be exposed to smoke from burning poison oak, which can cause serious, sometimes lethal, lung irritation.

Allergic dermatitis caused by exposure to urushiol-bearing plants is not only very uncomfortable; it is nearly ubiquitous. With 85% of Americans likely to develop an allergic reaction to urushiol, it is the most common allergy in the country. Twenty-five to forty million Americans seek medical attention annually, and Rhus dermatitis accounts for 10% of the U.S.D.A. and U.S. Forestry Service's lost time.

While the itching of Rhus dermatitis can be ameliorated with any number of creams, antihistamine and steroidal treatments and home remedies, the better strategy is to avoid contact with urushiol-bearing plants altogether. Of course, while one can always wear long-sleeved shirts and long pants when in areas where urushiol-bearing plants may exist, this might make summertime activity rather uncomfortably warm. One can try to identify and avoid plants in the field (e.g., using identification cards). However, given their varying appearance and ability to camouflage themselves among other plants, urushiol-bearing plants can be extremely difficult to identify in the field. Accordingly, the average person will have great difficulty avoiding contact with the plants, and will be at risk of suffering the painful itching of Rhus dermatitis.

Accordingly, there remains a need for new methods to identify urushiol-bearing plants.

SUMMARY OF THE INVENTION

One aspect of the present invention is a method of detecting a urushiol-bearing plant, the method comprising:
dispensing a urushiol marking composition on a surface of the urushiol-bearing plant; then
detecting a visual change on the urushiol-bearing plant caused by the reaction of the urushiol marking composition with the urushiol borne by the urushiol-bearing plant.

The present invention is capable of providing a number of advantages over the prior art. For example, in certain aspects the present invention, urushiol-bearing plants can be identified en masse and in situ among other, more benign plants. In certain aspects of the invention, simple visual determinations of color changes can be used to identify urushiol-bearing plants, which can then be avoided, killed or removed. In certain aspects, the methods of the present invention can be practiced without the use of external substrates such as patches or swabs. Additional features and advantages of the invention will be set forth in the detailed description which follows and will be readily apparent to those skilled in the art from the description or recognized by practicing the invention as described in the written description and claims hereof.

It is to be understood that both the foregoing general description and the following detailed description are merely exemplary of the invention, and are intended to provide an overview or framework for understanding the nature and character of the invention as it is claimed.

DETAILED DESCRIPTION OF THE INVENTION

One aspect of the invention is a method of detecting a urushiol-bearing plant. The method comprises dispensing a urushiol marking composition on a surface of the urushiol-bearing plant; then detecting a visual change on the urushiol-bearing plant caused by the reaction of the urushiol marking composition. As used herein, a urushiol marking composition is a composition that can undergo a reaction with urushiol borne on a urushiol-bearing plant to cause a visual change. Particular urushiol marking compositions are described in more detail below.

In one embodiment of the invention, the dispensing of the urushiol marking composition is performed by spraying a solution or suspension of the urushiol marking composition on the urushiol-bearing plant. Conveniently, the solution or suspension can be sprayed over a wide area including both one or more urushiol-bearing plants and one or more other plants. The composition can be supplied as a concentrate, for example, which can be diluted or suspended in water for spraying. A squirt bottle, pressure sprayer or a hose-end sprayer can be used to spray the solution or suspension of the urushiol marking composition. Of course, in other embodiments of the invention the urushiol marking composition is dispensed in a different manner. For example, the urushiol marking composition can be provided as a powder, which can be sprinkled on the urushiol-bearing plants and optionally moistened with water.

For example, in one embodiment of the invention, the urushiol marking composition is provided as a premixed solution or suspension, and applied directly through, e.g., a spray bottle, a hose-end sprayer or a pressurized tank sprayer. This embodiment of the invention can be useful, for example, for home gardeners in treating relatively smaller coverage areas.

In another embodiment of the invention, the urushiol marking composition is provided by diluting a concentrated solution or suspension with water. The urushiol marking composition can then be applied through, e.g., a spray bottle, a hose-end sprayer or a pressurized tank sprayer. This embodiment of the invention can be useful, for example, for the larger coverage areas encountered by commercial garden services and park and public area maintenance organizations.

In another embodiment of the invention, the urushiol marking composition is provided by dissolving or suspending a granular or powder mixture in water. The urushiol marking composition can then be applied through, e.g., a hose end sprayer or a pressurized tank sprayer. This embodiment of the invention can be useful, for example, for the larger coverage areas encountered by commercial garden services and park and public area maintenance organizations.

In certain embodiments, the urushiol marking composition can be rinsed from the surface of any non-target plants after the detection of the visual change. Rinsing can prevent damage to non-target species that might occur at long exposure times to the urushiol marking compound.

In certain embodiments of the invention, the urushiol marking composition is selective for urushiol-bearing plants. Accordingly, in one embodiment of the invention, the urushiol marking composition is dispensed on one or more other (i.e., non-urushiol-bearing) plants in addition to the urushiol-bearing plant. In this embodiment of the invention, the other plants undergo substantially no visual change, or undergo a visual change that is substantially different (e.g., in color and/or intensity) than that undergone by the urushiol-bearing plant. According to this embodiment of the invention, the user can easily visually distinguish between the urushiol-bearing plant and other, more benign plants. In certain embodiments of the invention, for example when urushiol oil is present on the leaf surface, the visual change undergone by the urushiol-bearing plant can occur within less than about four hours, or even less than about an hour after the dispensing. In other embodiments of the invention, for example when the urushiol marking composition must penetrate the leaf surface in order to react with urushiol oil, the visual change can occur at longer times, e.g., after a period in the range of 24 hours to a week.

In one embodiment of the invention, the urushiol-bearing plant is removed or killed after the visual change is detected. According to this embodiment of the invention, a user can use the methods of the present invention to determine which plants in a particular outdoor area bear urushiol, then remove or kill those particular plants while leaving unmolested other, more benign plants. Accordingly, the present invention can provide, for example, urushiol-bearing plant-free yards, gardens, forest areas, sidewalks, parking lots, playgrounds, parks and hiking trails. In other embodiments of the invention, the urushiol-bearing plant is not removed or killed, but rather merely avoided by a person walking or working nearby.

The methods of the present invention can be used to detect virtually any urushiol-bearing plant. For example, in certain embodiments of the invention, the urushiol-bearing plant is poison ivy, poison oak or poison sumac. In other embodiments of the invention, the urushiol-bearing plant is *Toxicodendron diversilobum* (poison oak), *Toxicodendron radicans* including ssp. *divaricatum* (poison ivy), *Toxicodendron rydbergii* (Rocky Mountain poison oak), *Toxicodendron vernix* (poison sumac), *Toxicodendron vernicifluum*, (Japanese lacquer tree), *Magnifera indica* (mango tree), *Anacardium occidentale* (cashew tree) *Gluta renghas* (Rengas tree),*Melanorrhoea usitata* (Burmese lacquer tree), *Metopium toxiferum* or *Comocladia dodnaea* (both Caribbean shrubs), *Semecarpus anacardium* (India marking nut tree), *Ginkgo biloba*, or a member of the Proteaceae family.

As described above, a urushiol marking composition is a composition that can undergo a reaction with urushiol borne on a urushiol-bearing plant to cause a visual change. The urushiol marking composition can include any of a number of chemical species that react with urushiol to provide a visual change. For example, in one embodiment of the invention, the urushiol marking composition includes a ferric compound. Ferric compounds react with urushiol to cause a darkening of color. Ferric salts such as ferric sulfate, ferric ammonium citrate, ferric ammonium sulfate, ferric nitrate and ferric chloride can be used in the urushiol marking composition. Such salts can be formulated in high concentrations in aqueous media, and therefore can be dispensed as relatively concentrated compositions and provide a marked color change upon contact with a urushiol-bearing plant. The ferric compound can be present in the composition, for example, at a concentration in the range of about 0.5 wt % to about 10 wt %.

In one embodiment of the invention, the urushiol marking composition has as its ferric compound ferric nitrate or ferric chloride. For example, the urushiol marking composition can be an aqueous ferric nitrate solution having a ferric nitrate or ferric chloride concentration in the range of about 1 wt % to about 10 wt % (e.g., about 3 wt % to about 7 wt %, or about 5 wt % to about 10 wt %) optionally with one or more additional chemical species added. At such concentrations, ferric nitrate solutions can provide sufficient color response (e.g., spotting of the leaf and a darkening and curling of leaf edges) without causing unacceptable damage to other plant species.

In another embodiment of the invention, the urushiol marking composition has as its ferric compound a chelated iron compound. For example, the chelated iron compound can be iron(III) diethylenetriameinepentaacetic acid, or iron(III) ethylenediaminetetraacetic acid. . For example, the urushiol marking composition can be an aqueous ferric nitrate solution having a chelated iron compound concentration in the range of about 1 wt % to about 10 wt % (e.g., about 3 wt % to about 7 wt %, or about 5 wt % to about 10 wt %) optionally with one or more additional chemical species added. While not wishing to be bound by theory, the inventor surmises that chelated iron can more easily penetrate any waxy coating on the leaves of the urushiol oil-bearing plant.

Color-forming reactions of metallic compounds with catechols such as urushiol are described in U.S. Pat. No. 4,472, 507, which is hereby incorporated by reference in its entirety. Moreover, catechol concentrations have been measured using a reagent mixture of 30 parts 0.1 M sodium carbonate-0.1 M sodium hydrogen carbonate buffer, 10 parts of 5% polyoxyethylene monlauryl ether, 6 parts of 1 mM ferric ammonium sulfate, 6 parts of 1 mM phenylfluorone in methanol, and 38 parts water. Catechol concentrations were determined by absorbance at 630 nm and comparing to a catechol standard curve (the measured molar extinction coefficient was 22,600 $M^{-1}cm^{-1}$). See Yin Tao et al., Oxidation of Benzene to Phenol, Catechol, and 1,2,3-Trihydroxybenzene by Toluene 4-Monooxygenase of *Pseudomonas mendocina* KR1 and Toluene 3-Monooxygenase of *Ralstonia Pickettii* PKO1, Appl. and Env. Microbiol., July 2004, 3814-3820, and Fujita, Y. et al., A color reaction of 1,2 diphenols based on colored complex formation with phenylfluorone and iron (III) and its application to the assay of catecholamines in pharmaceutical preparations, *Chem. Pharm. Bull.*, 33, 5385-5392 (1985) each of which is hereby incorporated by reference in its entirety.

In certain embodiments of the invention, the urushiol marking composition includes an enzyme that catalyzes the reaction of urushiol. For example, in one embodiment of the invention, the urushiol marking composition includes an enzyme that catalyzes the oxidation of the catechol moiety of the urushiol to form a 1,2-benzoquinone moiety. For example, the urushiol marking composition can include a catechol oxidase, a tyrosinase, a laccase or a polyphenol oxidase. Reaction of catechols with such enzymes can cause a darkening of color; such reactions are responsible for the darkening of interior fruit tissue when it is exposed to air. Enzymatic systems can be provided as suitably buffered solutions, along with any co-reactants necessary to cause the desired reaction. As an example of an enzymatic reaction, U.S. Pat. No. 4,259,318, which is hereby incorporated by reference in its entirety, describes the reaction of laccase with urushiol.

In certain embodiments of the invention in which an reaction (e.g., enzymatic or other oxidation) forms 1,2-benzoquinone, an organic amine can also be included in the urushiol marking composition. Organic amines can react with 1,2-benzoquinones to form colored compounds that will tend to increase the intensity of the color change. For example, a catechol can be oxidized enzymatically (e.g., using tyrosinase) to form a 1,2-benzoquinone, which can react with an amine such as proline to form a strongly colored compound. See Howard S. Mason and E. W. Patterson, The Reaction of Quinones with Protamine and Nucleoprotamine: N-Terminal Proline, *J. Biol. Chem*, 212(1), 485-496 (1955), which is hereby incorporated herein by reference in its entirety. In another example, a stable pink adduct ($A_{max}$=520 nm, molar extinction coefficient=5000 $M^{-1}cm^{-1}$) is formed when diethylamine is reacted with enzymatically-produced 1,2-benzoquinone at near-neutral pH. See S. Uchiyama et al., Formation of a stable adduct between 1,2-benzoquinone and dimethylamine and its application to the spectrophotometric determination of 1,2-benzoquinone, *Anal. Chim. Acta,* 351 (1-3), 259-264 (1997), which is hereby incorporated herein by reference in its entirety. The enzymatic oxidation of 4-methylcatechol by polyphenol oxidase followed by reaction with 4-amino-N,N-diethylaniline forms a deep blue ($A_{max}$=617 nm) adduct having a molar extinction coefficient of 11,080 $M^{-1}cm^{-1}$. Luca Valgimigli et al., Photometric assay for polyphenol oxidase activity in olives, olive pastes and virgin olive oils, *J. Amer. Oil Chemists' Soc.*, 78(12), 1245-1248 (2001), which is hereby incorporated herein by reference in its entirety. See also U.S. Pat. No. 5,588,972, which is hereby incorporated by reference in its entirety. Chemical oxidants can also be used to generate 1,2-benzoquinones for reaction as described above.

In certain embodiments of the invention, the urushiol marking composition includes a cyclodextrin. Cyclodextrins can complex urushiol, and can increase the response of colorimetric reactions and complexations of other compounds therewith. Moreover, the use of a cyclodextrin can impart some haziness or chalkiness in appearance to the urushiol-bearing plant, which can be an important visual change (e.g., a haziness or a lightening in color) on its own, and/or can provide a lighter background against which to visualize a color change due to another reactant. The use of cyclodextrins with urushiol is described in U.S. Pat. No. 5,767,109 and U.S. Patent Application Publication 2006/0147341, each of which is hereby incorporated herein by reference in its entirety. Cyclodextrins (e.g., γ-cyclodextrin) can be especially useful when the urushiol marking composition includes a ferric compound such as ferric nitrate.

Other additives can be used in the urushiol marking composition to enhance the visual change. For example, soap compounds, alcohol compounds, lecithin (e.g., liquid lecithin), amines (e.g., dimethylamine), surfactants (e.g., WETCIT and OROBOOST, surfactants available from ORO AGRI), dextrin, cyclodextrins (e.g., γ-cyclodextrin) and acids (e.g., acetic acid) can be used to increase enhance the visual change. Such additives can be especially useful when the urushiol marking composition includes a ferric compound such as ferric nitrate. For example, a lower alcohol such as methanol, ethanol or isopropanol can be added at levels up to 20 wt %. OROBOOST and WETCIT solutions can be added, for example, at levels in the 0.01 vol % to 2.0 vol % range (e.g., about 0.05 vol %). Concentrated acids such as acetic acid can be added, for example, at levels in the 5-100 drops/L range (e.g., about 3 drops/100 mL). In other examples, an acid such as acetic acid can be provided at up to about 10 wt %, up to about 5 wt %, or up to about 1 wt %. Dextrin can be added, for example, at levels in the 0.05 wt % to 2 wt % range (e.g. about 0.5 wt %). Cyclodextrins can be added, for example, in the 1-1000 wt. ppm range (e.g., about 200 wt. ppm).

In one embodiment of the invention, the urushiol marking composition includes a ferric salt at a concentration in the range of about 0.5 wt % to about 10 wt %; water at a concentration in the range of about 75 wt % to about 99.5 wt %. In certain embodiments, the urushiol marking composition can further include one or more of the following: a lower alcohol (e.g., isopropanol) at concentration up to about 10 wt %; an acid (e.g., acetic acid) at concentrations up to about 10 wt %; a cyclodextrin (e.g., γ-cyclodextrin) at a concentration up to about 1000 wt. ppm; and/or a surfactant (e.g., lecithin or OROBOOST solution) at a concentration up to about 2 vol %; phenylfluorone at a concentration up to about 0.5 wt %. The ferric salt can be, for example, ferric nitrate or ferric chloride. In certain embodiments, the urushiol marking composition only includes one of cyclodextrin and lower alcohol.

In one embodiment of the invention, the urushiol marking composition consists essentially of a ferric salt at a concentration in the range of about 0.5 wt % to about 10 wt %; water at a concentration in the range of about 75 wt % to about 99.5 wt %. In certain embodiments, the urushiol marking composition can further include one or more of the following: a lower alcohol (e.g., isopropanol) at concentration up to about 10 wt %; an acid (e.g., acetic acid) at concentrations up to about 1 wt %; a cyclodextrin (e.g., γ-cyclodextrin) at a concentration up to about 1000 wt. ppm; and/or a surfactant (e.g., lecithin or OROBOOST solution) at a concentration up to about 2 vol %; phenylfluorone at a concentration up to about 0.5 wt %, as described above.

The visual change used to detect the urushiol-bearing plant can take many forms. For example, the visual change is a color change, such as a darkening in color or a lightening in color as described above. The detection of the visual change can comprise visually detecting a change in color of at least part of the urushiol-bearing plant under ambient light conditions. Alternatively, additional visible light (e.g. from a floodlight or a flashlight) can be provided for detection of the color change. The color change can be discontinuous across the leaf, for example, taking the form of spots or speckles, or browning along the leaf edges. The visual change can additionally or alternatively include curling of leaf edges, optionally with a discoloration (e.g., browning) along the curled edges.

In other embodiments of the invention, fluorescence is used to detect the urushiol-bearing plant. For example, in one embodiment of the invention the detection of the visual change comprises shining low wavelength radiation (e.g., ultraviolet radiation substantially above ambient levels) on the urushiol-bearing plant; and visually detecting higher wavelength radiation (e.g., visible radiation) emitted by the urushiol-bearing plant in response to the exposure to the low wavelength radiation.

In certain embodiments, the visual change can be enhanced by post treatment with another chemical species. Accordingly, the methods described herein can further comprise dispensing a change enhancing composition on the surface of the plant before detecting the visual change. In one embodiment, the change enhancing composition is a basic aqueous solution, for example, aqueous lower organic amine. Use of an aqueous lower organic amine can be especially beneficial in conjunction with ferric salt-based urushiol marking compositions. In one embodiment, the change enhancing composition is an aqueous solution of dimethylamine (e.g., in the range of about 0.1 wt % to about 5 wt %). In certain embodiments, there is a delay between dispensing the urushiol marking composition on the plant and dispensing the change enhancing composition on the plant. The delay can be, short, for example, in the range of 1 min-1 hour; or relatively long (e.g., in the range of 18 hours-48 hours). Of course, other delay periods can be used. While not intending to be bound by theory, the inventor surmises that the delay allows the urushiol marking composition to penetrate the leaf surface before the change enhancing composition is applied.

EXAMPLES

Testing was conducted in the Omaha, Nebr. area in 2008, and in the Jackson, Minn. area in 2009. Individual test plots varied in size from about 1 ft$^2$-3 ft$^2$, and included one poison ivy plant and at least one plant from a non-target species. Solutions were applied using squirt/spray bottles, saturating all leaf surfaces within the test plot.

Solutions of ferric nitrate (5 wt %) in water reacted nearly instantaneously with poison ivy plants bearing urushiol oil on their leaves, exhibiting significant darkening of the oil as speckling and spotting on the leaf surfaces. When the leaf surfaces did not have oil on them, reaction with the ferric nitrate took several days, presumably because the solution had to penetrate the leaf surface to react with urushiol oil. After a period of three weeks, ferric nitrate solutions (e.g., 5 wt %, 1 wt %) caused large blackish spots to appear over 10-50% of the poison ivy leaf surfaces, while causing relatively little discoloration of non-target plants (e.g., no reaction after three weeks at 1 wt % ferric nitrate concentration). A 6 wt % ferric nitrate solution exhibited no reaction with non-target plants after two days.

To 100 mL of a solution of 5 wt % ferric nitrate was added 0.5 g dextrin; the resulting solution was applied as described above. After one hour, dark speckles appeared on the poison ivy surfaces. After forty-eight hours, increased speckling was observed, accompanied by browning of the leaf surfaces; little to no damage was noted on non-target species. After one week, brown spotting and yellowing of the poison ivy leaf surfaces were observed, along with curling and browning of the poison ivy leaf edges. Again, little to no damage to non-target species was observed.

To 100 mL of a solution of 6 wt % ferric nitrate was added 3 drops glacial acetic acid; the resulting solution was applied as described above. Seven hours after application, brown spotting was observed on the poison ivy leaves, but not on non-target plant leaves. After two days, additional spotting was observed on the poison ivy leaves, with no reaction on non-target plant leaves.

To a 100 mL solution of 5 wt % ferric nitrate was added 20 mg γ-cyclodextrin; the resulting solution was applied as described above. Twenty-four hours after application, the poison ivy leaves were brown and curled at the edges and slightly brown on the rest of their surfaces. After 48 hours, the leaves were brown with black speckles on their surfaces and somewhat droopy. After 10 days, droplet-sized black speckles remained on the leaves. After 22 days, the leaves had black and brown spots covering ~10-20% of the surfaces. After 26 days, the black and brown areas had further grown in size.

To a 100 mL solution of 5 wt % ferric nitrate was added 20 mg γ-cyclodextrin and one drop OROBOOST; the resulting solution was applied as described above. Twenty-four hours after application, the poison ivy leaves were brown and curled at the edges and speckled black and glossy on their surfaces. After 48 hours, the leaves were speckled black and droopy. After 10 days, droplet-sized black speckles remained on the leaves, and the edges of the leaves were curled and brown. After 22 days, the leaves remained curled, with black spotting and some browning.

To 100 mL solutions of 5 wt % ferric nitrate was added vinegar ((a) 0.5 mL, (b) 1 mL or (c) 5 mL; 5% acidity); the resulting solutions were applied as described above. Twenty-four hours after application, the edges of all leaves had browned and curled, with black speckling on the leaf surfaces; the reactions were most visible for solutions (a) and (c). After 48 hours, the reaction appeared similar, but no damage to benign plants was observed. After 10 days, the leaves exhibited highly visible edge browning with black speckling; the reactions were most visible for solutions (b) and (c). After 26 days, the solution (a) and (c) examples had the most visible black spots.

To a 100 mL solution of 5% ferric nitrate was added 20 mg cyclodextrin and 1 mL vinegar (5% acidity). After three days, slight edge darkening was visible. After 15 days, some reaction was visible.

To 100 mL solutions of 5% ferric chloride was added (a) 20 mg γ-cyclodextrin; (b) 20 mg γ-cyclodextrin and 5 mL isopropanol; (c) 20 mg γ-cyclodextrin and 3 drops OROBOOST; and (d) 20 mg γ-cyclodextrin, 5 mL isopropanol and 3 drops OROBOOST. The solutions were applied as described above. All solutions exhibited initial darkening of damaged areas of the leaves. After 24 hours, leaves were somewhat wrinkled for solution (a), and black spotting was visible for solutions (b), (c) and (d). After 48 hours, leaves treated with solutions (a) and (d) exhibited slight black spotting, and leaves treated with solutions (b) and (c) exhibited larger and darker black spots. After three days, the black spots on leaves treated with solution (d) had darkened.

To 100 mL solutions of 5 wt % ferric nitrate was added phenylfluorone ((a) spatula tip; (b) a half-spatula or (c) a full spatula); the resulting solutions were applied as described above. As these solutions were more darkly colored, they were also tested on three patches of lawn grass. After 24 hours, some black spotting was visible, with no spotting on the grass. After 48 hours, a glossy sheen and some browning were apparent on leaves treated with solutions (b) and (c), while leaves treated with solution (a) showed browned areas with larger black spotting. After three days, leaves treated with solution (a) had significant areas of damage (black and brown areas), leaves treated with solution (b) showed leaf curl with a glossy sheen and some browning. Leaves treated with solution (c) showed some browning and leaf gloss too, but slight damage to the grass was also evident.

5% Ferric chloride solutions were applied as described above. After a five minute delay, (a) dimethylamine (1%) or (b) dimethylamine/isopropanol (5 mL isopropanol in 100 mL dimethylamine) solutions were applied as described above. After 24 hours, some black spotting was visible on leaves treated with solution (a). After 48 hours, black spotting was visible on leaves treated with either solution, but more spotting was visible for solution (a).

5% Ferric chloride solutions were applied as described above. After a 24 hour delay, (a) dimethylamine (1%) or (b) dimethylamine/isopropanol (5 mL isopropanol in 100 mL dimethylamine) solutions were applied as described above. Immediately at application of solutions (a) or (b), black spotting was visible. After an additional 24 hours, black spots were very visible, and the edges of leaves treated with solution (b) were brown.

5% Ferric nitrate solutions were applied as described above. After a 24 hour delay, (a) dimethylamine (1%) or (b) dimethylamine/isopropanol (5 mL isopropanol in 100 mL dimethylamine) solutions were applied as described above. Immediately at application of solutions (a) or (b), leaf edge browning was visible. After an additional 24 hours, the edge browning had become more visible, with mid-vein browning for solution (a) and black spotting for solution (b).

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A method of detecting a urushiol-bearing plant, the method comprising:
   spraying a solution or a suspension of a urushiol marking composition comprising a ferric compound over an area that includes the urushiol-bearing plant and one or more non-urushiol-bearing plants, thereby applying the urushiol marking composition on the urushiol-bearing plant and on the one or more non-urushiol-bearing plants, wherein the one or more non-urushiol-bearing plants undergo substantially no visual change, or undergo a visual change that is substantially different than that undergone by the urushiol-bearing plant; then
   detecting a visual change on the urushiol-bearing plant caused by a reaction of the urushiol marking composition with the urushiol borne by the urushiol-bearing plant, wherein the detecting is performed in the absence of a cyclodextrin.

2. The method of claim 1, further comprising, after detecting the visual change, removing or killing the urushiol-bearing plant.

3. The method of claim 1, further comprising, after detecting the visual change, rinsing the urushiol marking composition from the one or more non-urushiol-bearing plants.

4. The method of claim 1, wherein the urushiol-bearing plant is poison ivy, poison oak or poison sumac.

5. The method of claim 1, wherein the ferric compound is ferric nitrate or ferric chloride.

6. The method of claim 5, wherein the ferric chloride or ferric nitrate is present at a concentration in the range of about 1 wt % to about 10 wt % in the urushiol marking composition.

7. The method of claim 5, wherein the ferric chloride or ferric nitrate is present at a concentration in the range of about 3 wt % to about 7 wt % in the urushiol marking composition.

8. The method of claim 1, wherein the urushiol marking composition further comprises one or more additives selected from the group consisting of soap compounds, alcohol compounds, lecithin, amines, surfactants, dextrin, and acids.

9. The method of claim 1, wherein the visual change comprises a color change.

10. The method of claim 9, wherein the visual change comprises leaf curling.

11. The method of claim 1, wherein the detection of the visual change comprises visually detecting a change in color of at least part of the urushiol-bearing plant under ambient light conditions.

12. The method of claim 1, further comprising, before detecting the visual change, dispensing a change-enhancing composition on the urushiol-bearing plant, the change-enhancing composition comprising dimethylamine.

13. A method of detecting a urushiol-bearing plant, the method consisting essentially of:
   spraying a solution or a suspension of a urushiol marking composition comprising a ferric compound over an area that includes the urushiol-bearing plant and one or more non-urushiol-bearing plants, thereby applying the urushiol marking composition on the urushiol-bearing plant and on the one or more non-urushiol-bearing plants; and
   then
   detecting a visual change on the urushiol-bearing plant caused by a reaction of the urushiol marking composition with the urushiol borne by the urushiol-bearing plant, the detecting being performed in the absence of a cyclodextrin; and
   after detecting the visual change, removing or killing the urushiol-bearing plant.

14. The method of claim 13, wherein the ferric compound is ferric chloride or ferric nitrate present at a concentration in the range of about 3 wt % to about 7 wt % in the urushiol marking composition.

15. A method of detecting a urushiol-bearing plant, the method comprising:
   spraying a solution or a suspension of a urushiol marking composition comprising a ferric compound over an area that includes the urushiol-bearing plant and one or more non-urushiol-bearing plants, thereby applying the urushiol marking composition on the urushiol-bearing plant and on the one or more non-urushiol-bearing plants, wherein the one or more non-urushiol-bearing plants undergo substantially no visual change, or undergo a visual change that is substantially different than that undergone by the urushiol-bearing plant; and
   dispensing a change-enhancing composition on the urushiol-bearing plant, the change-enhancing composition comprising dimethylamine; then
   detecting a visual change on the urushiol-bearing plant caused by a reaction of the urushiol marking composition with the urushiol borne by the urushiol-bearing plant.

16. The method of claim 15, wherein the ferric compound is ferric nitrate or ferric chloride.

17. The method of claim 16, wherein the ferric chloride or ferric nitrate is present at a concentration in the range of about 1 wt % to about 10 wt % in the urushiol marking composition.

18. The method of claim 15, wherein the detection of the visual change comprises visually detecting a change in color of at least part of the urushiol-bearing plant under ambient light conditions.

19. The method of claim 15, wherein the urushiol marking composition further comprises one or more additives selected from the group consisting of soap compounds, alcohol compounds, lecithin, amines, surfactants, dextrin, and acids.

* * * * *